US00PP21320P2

(12) United States Plant Patent
Arts

(10) Patent No.: US PP21,320 P2
(45) Date of Patent: Sep. 28, 2010

(54) ***HYDRANGEA* PLANT NAMED 'AGRIHYDRAACHT'**

(50) Latin Name: *Hydrangea hybrida*
Varietal Denomination: Agrihydraacht

(75) Inventor: Niels Arts, Aalsmeer (NL)

(73) Assignee: Agriom B.V., De Kwakel (NL)

( * ) Notice: Subject to any disclaimer, the term of this patent is extended or adjusted under 35 U.S.C. 154(b) by 0 days.

(21) Appl. No.: 12/455,062

(22) Filed: May 27, 2009

(51) Int. Cl.
*A01H 5/00* (2006.01)

(52) U.S. Cl. ..... Plt./250

(58) Field of Classification Search ..... Plt./250
See application file for complete search history.

*Primary Examiner*—Susan B McCormick Ewoldt
(74) *Attorney, Agent, or Firm*—C. A. Whealy

(57) ABSTRACT

A new and distinct cultivar of *Hydrangea* plant named 'Agrihydraacht', characterized by its upright and mounded plant habit; strong and sturdy stems; freely branching habit; large inflorescences with white and bright blue bi-colored flowers.

1 Drawing Sheet

Botanical designation: *Hydrangea hybrida.*
Cultivar denomination: 'Agrihydraacht'.

BACKGROUND OF THE INVENTION

The present invention relates to a new and distinct cultivar of *Hydrangea* plant, botanically known as *Hydrangea hybrida* and hereinafter referred to by the name 'Agrihydraacht'.

The new *Hydrangea* plant is a product of a planned breeding program conducted by the Inventor in Aalsmeer, The Netherlands. The objective of the breeding program was to create new freely branching *Hydrangea* cultivars with strong and sturdy stems, large inflorescences and attractive flower color.

The new *Hydrangea* plant originated from a cross-pollination made by the Inventor on Apr. 15, 2003 in Aalsmeer, The Netherlands, of a proprietary selection of *Hydrangea hybrida* identified as code number 201018, not patented, as the female, or seed, parent with a proprietary selection of *Hydrangea hybrida* identified as code number 99112-03, not patented, as the male, or pollen, parent. The new *Hydrangea* was discovered and selected by the Inventor as a single flowering plant from within the progeny of the stated cross-pollination in a controlled greenhouse environment in Glandorf, Germany on Mar. 15, 2005.

Asexual reproduction of the new *Hydrangea* plant by vegetative cuttings in a controlled environment in Glandorf, Germany since Mar. 15, 2005, has shown that the unique features of this new *Hydrangea* plant are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Agrihydraacht'. These characteristics in combination distinguish 'Agrihydraacht' as a new and distinct cultivar of *Hydrangea:*

1. Upright and mounded plant habit.
2. Strong and sturdy stems.
3. Freely branching habit.
4. Large inflorescences with white and bright blue bi-colored flowers.

Plants of the new *Hydrangea* differ from plants of female parent selection primarily in flower color as plants of the female parent selection have white and purple bi-colored flowers. In addition, plants of the new *Hydrangea* are more freely branching than plants of the female parent selection.

Plants of the new *Hydrangea* differ from plants of male parent selection primarily in flower coloration as sepals of plants of the male parent selection have narrower white-colored margins.

Plants of the new *Hydrangea* can be compared to plants of the *Hydrangea* 'Tivoli', not patented. Plants of the new *Hydrangea* differ from plants of 'Tivoli' in the following characteristics:

1. Plants of the new *Hydrangea* have shorter internodes than plants of 'Tivoli'.
2. Plants of the new *Hydrangea* have shorter leaves than plants of 'Tivoli'.
3. Plants of the new *Hydrangea* have smaller inflorescences with fewer flowers per inflorescence than plants of 'Tivoli'.
4. Plants of the new *Hydrangea* and 'Tivoli' differ in flower color as plants of 'Tivoli' have purple and light pink bi-colored flowers.

BRIEF DESCRIPTION OF THE PHOTOGRAPH

The accompanying colored photograph illustrates the unique appearance of the new *Hydrangea* plant, showing the colors as true as it is reasonably possible to obtain in colored reproductions of this type. Colors in the photograph may differ from the color values cited in the detailed botanical description which accurately describe the colors of the new *Hydrangea* plant. The photograph comprises a side perspective view of a typical flowering plant of 'Agrihydraacht' grown in a container.

DETAILED BOTANICAL DESCRIPTION

Plants used in the aforementioned photograph and in the following description were grown during the winter in De Kwakel, The Netherlands, in 15-cm containers in a glass-covered greenhouse and under conditions which closely approximate commercial *Hydrangea* production conditions. During the production of the plants, day and night temperatures averaged 17° C. Plants of the new *Hydrangea* were one year old when the photograph and description were taken. In the following description, color references are made to The Royal Horticultural Society Colour Chart, 1995 Edition, except where general terms of ordinary dictionary significance are used.

Botanical description:

*Hydrangea hybrida.*—'Agrihydraacht'.

Parentage:

*Female, or seed, parent.*—Proprietary selection of *Hydrangea hybrida* identified as code number 201018, not patented.

*Male, or pollen, parent.*—Proprietary selection of *Hydrangea hybrida* identified as code number 99112-03, not patented.

Propagation:

*Type cutting.*—By vegetative cuttings.

*Time to initiate roots, summer.*—About 14 days at temperatures of 23° C.

*Time to initiate roots, winter.*—About 18 days at temperatures of 18° C.

*Time to produce a rooted young plant, summer.*—About four weeks at temperatures of 23° C.

*Time to produce a rooted young plant, winter.*—About five weeks at temperatures of 18° C.

*Root description.*—Thick; whitish brown in color.

*Rooting habit.*—Freely branching; dense.

Plant description:

*Form growth habit.*—Upright and mounded plant habit; inverted triangle; strong and sturdy lateral branches; vigorous growth habit.

*Plant height.*—About 30 cm to 40 cm.

*Plant diameter or area of spread.*—About 40 cm.

*Branching habit.*—Freely branching habit; when pinched, about seven lateral branches develop per plant.

*Lateral branches.*—Length: About 30 cm. Diameter: About 4 mm. Internode length: About 5 cm. Texture: Smooth, glabrous. Strength: Strong and sturdy. Color: Close to 145A tinted with close to 187A.

Foliage description:

*Arrangement.*—Opposite, simple.

*Length.*—About 9 cm.

*Width.*—About 7 cm.

*Shape.*—Ovate.

*Apex.*—Acute to acuminate.

*Base.*—Obtuse.

*Margin.*—Dentate to serrate.

*Texture, upper and lower surfaces.*—Rugose, glabrous.

*Venation pattern.*—Pinnate.

*Color.*—Developing leaves, upper surface: Close to 137A. Developing leaves, lower surface: Close to 146A. Fully expanded leaves, upper surface: Close to 137A; venation, close to 148C. Fully expanded leaves, lower surface: Close to 137C; venation, close to 148C.

*Petiole.*—Length: About 1.5 cm. Diameter: About 3 mm. Texture, upper and lower surfaces: Smooth, glabrous. Color, upper and lower surfaces: Close to 148C.

Flower description:

*Flower type and habit.*—Single sterile and fertile flowers arranged on terminal panicles; panicles globular in shape; flowers face upright to outward.

*Fragrance.*—None detected.

*Natural flowering season.*—Continuous flowering during the summer in Northern Europe.

*Flower longevity.*—Sterile flowers last about four months on the plant; fertile flowers last about one month on the plant; flowers not persistent.

*Quantity of flowers.*—Freely flowering; about 40 to 60 sterile flowers per panicle and about 30 fertile flowers per panicle.

*Panicle height.*—About 6 cm.

*Panicle diameter.*—About 12 cm.

*Sterile flower diameter.*—About 3.5 cm.

*Sterile flower depth (height).*—About 1 cm.

*Fertile flower diameter.*—About 6 mm.

*Fertile flower depth (height).*—About 5 mm.

*Flower buds.*—Length: About 3 mm. Diameter: About 3 mm. Shape: Globular. Color: Close to 144A.

*Petals, sterile flowers only, fertile flowers without petals.*—Arrangement: About four in a single whorl. Length: About 3 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 145C. Fully opened, upper surface: Close to 145D. Fully opened, lower surface: Close to 96D.

*Sepals, sterile flowers.*—Quantity per flower: About four or five in a single whorl. Length: About 1.5 cm. Width: About 1.8 cm. Shape: Deltoid. Apex: Retuse. Base: Cuneate. Margin: Entire. Texture, upper surface: Smooth, glabrous. Texture, lower surface: Rugose, glabrous. Color, upper surface: Close to 98A; towards the margins, close to 155B. Color, lower surface: Close to 98B; towards the margins, close to 155B.

*Sepals, fertile flowers.*—Quantity per flower: About four or five in a single whorl. Length: About 3 mm. Width: About 2 mm. Shape: Ovate. Apex: Acute. Base: Obtuse. Margin: Entire. Texture, upper and lower surfaces: Smooth, glabrous. Color, upper surface: Close to 100A. Color, lower surface: Close to 100B.

*Pedicels, sterile flowers.*—Angle: About 45° from vertical. Strength: Strong. Length: About 2 cm. Diameter: About 1.5 mm. Texture: Smooth, glabrous. Color: Close to 177B.

*Pedicels, fertile flowers.*—Angle: Mostly upright. Strength: Moderately strong. Length: About 5 mm. Diameter: About 1 mm. Texture: Smooth, glabrous. Color: Close to 119A.

*Reproductive organs, fertile flowers only; sterile flowers without reproductive organs.*—Stamens: Quantity per flower: About eight. Anther shape: Conical. Anther length: About 1 mm. Anther color: Close to 145D and 130C. Pollen amount: Abundant. Pollen color: Close to 145D. Pistils: Pistil quantity per flower: About three. Pistil length: About 1 mm. Stigma shape: Oval.

Stigma color: Close to 145D. Style length: About 1 mm. Style color: Close to 145C. Ovary color: Close to 145C.

*Seeds.*—Length: About 0.5 mm. Diameter: About 0.1 mm. Color: Close to 200C.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 3° C. to about 38° C.

It is claimed:

1. A new and distinct *Hydrangea* plant named 'Agrihydraacht' as illustrated and described.

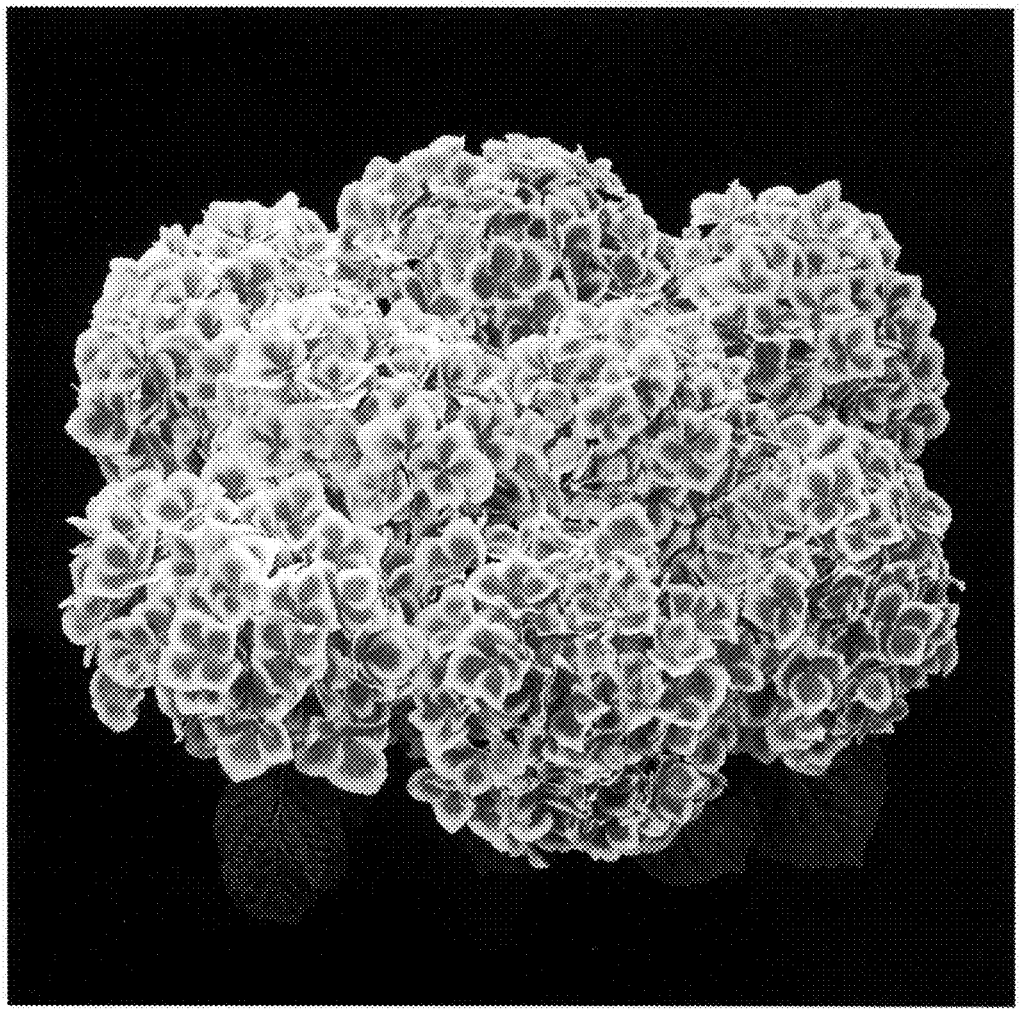

* * * * *